(12) United States Patent
Simmons

(10) Patent No.: US 11,464,400 B2
(45) Date of Patent: Oct. 11, 2022

(54) ENDOSCOPE MOUNTABLE VISUALIZATION DEVICE QUICK-CONNECT/RELEASE HANDLE ATTACHMENT MECHANISM

(71) Applicant: Cook Medical Technologies LLC, Bloomington, IN (US)

(72) Inventor: Victor Anthony Simmons, Mt. Airy, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 487 days.

(21) Appl. No.: 16/363,491

(22) Filed: Mar. 25, 2019

(65) Prior Publication Data

US 2019/0216303 A1    Jul. 18, 2019

Related U.S. Application Data

(62) Division of application No. 14/863,732, filed on Sep. 24, 2015, now Pat. No. 10,238,272.

(Continued)

(51) Int. Cl.
*A61B 1/012* (2006.01)
*A61B 1/00* (2006.01)

(52) U.S. Cl.
CPC ........ *A61B 1/0125* (2013.01); *A61B 1/00128* (2013.01)

(58) Field of Classification Search
CPC .............. A61B 1/0125; A61B 1/00128; A61B 1/00064; A61B 1/0014; A61B 2017/347; A61B 2017/00424; Y10T 24/44017
See application file for complete search history.

(56) References Cited

U.S. PATENT DOCUMENTS 5,171,245 A * 12/1992 Cezana .............. A61B 17/3417
606/53
5,626,553 A   5/1997 Frassica et al.
(Continued)

FOREIGN PATENT DOCUMENTS

EP          0 664 991 A2    8/1995
JP       2002/078668 A      3/2002
(Continued)

OTHER PUBLICATIONS

International Search Report and Written Opinion dated Aug. 2, 2010 for International Application No. PCT/US2010/032398.
(Continued)

*Primary Examiner* — Alexandra L Newton
(74) *Attorney, Agent, or Firm* — Crowell & Moring LLP

(57) ABSTRACT

An endoscope can include an elongate, manipulable shaft with a distal-end visualization element and a handle body comprising at least one control surface for manipulating a distal region of the shaft, where the handle body includes a passage through which a length of the shaft is passable, and where the handle body includes a novel connection structure configured for firmly, securely, and removably mounting the handle to a channel of another endoscope in a manner axially aligning the passage with the channel to provide a path of communication for the shaft. A dual medical endoscope system can be constructed including a first and a second medical endoscope, where the first endoscope comprises an accessory channel with a proximal mounting port providing access thereto, and where the second endoscope comprises a handle body that is securely and removably attached to the proximal mounting port.

10 Claims, 11 Drawing Sheets

Related U.S. Application Data

(60) Provisional application No. 62/056,904, filed on Sep. 29, 2014.

(56) References Cited

U.S. PATENT DOCUMENTS

| | | | |
|---|---|---|---|
| 5,863,286 A | 1/1999 | Yabe | |
| 6,110,104 A | 8/2000 | Suzuki et al. | |
| 7,922,650 B2 | 4/2011 | McWeeney et al. | |
| 8,460,176 B2 | 6/2013 | McGrath | |
| 2003/0028096 A1 | 2/2003 | Niwa et al. | |
| 2004/0158127 A1 | 8/2004 | Okada | |
| 2004/0230268 A1 | 11/2004 | Huff et al. | |
| 2005/0033319 A1 | 2/2005 | Gambale | |
| 2005/0182292 A1 | 8/2005 | Suzuki | |
| 2005/0222494 A1 | 10/2005 | Prescott | |
| 2005/0267417 A1 | 12/2005 | Secrest | |
| 2006/0252993 A1 | 11/2006 | Freed et al. | |
| 2006/0269442 A1 | 11/2006 | Nguyen | |
| 2007/0270640 A1 | 11/2007 | Dimitriou et al. | |
| 2007/0276180 A1* | 11/2007 | Greenburg | A61B 90/50 600/106 |
| 2008/0097159 A1 | 4/2008 | Ishiguro | |
| 2008/0242930 A1* | 10/2008 | Hanypsiak | A61B 17/3421 600/114 |
| 2009/0030443 A1* | 1/2009 | Buser | A61B 17/3496 606/185 |
| 2009/0088600 A1* | 4/2009 | Meloul | A61B 1/00137 600/104 |
| 2010/0087705 A1 | 4/2010 | Byers | |
| 2010/0198006 A1* | 8/2010 | Greenburg | A61B 1/012 600/104 |
| 2010/0228084 A1 | 9/2010 | Sato et al. | |
| 2010/0280311 A1* | 11/2010 | McGrath | A61B 1/00137 600/104 |
| 2011/0099773 A1* | 5/2011 | Golden | F16B 2/12 24/457 |
| 2013/0217963 A1 | 8/2013 | Naito | |
| 2014/0114126 A1 | 4/2014 | Dresher | |
| 2014/0316200 A1 | 10/2014 | Maxwell | |
| 2015/0045618 A1* | 2/2015 | Yamada | A61B 1/00133 600/106 |
| 2015/0057537 A1 | 2/2015 | Dillon et al. | |
| 2016/0262601 A1* | 9/2016 | Viebach | A61B 1/00163 |

FOREIGN PATENT DOCUMENTS

| | | |
|---|---|---|
| JP | 2005296305 A | 4/2004 |
| JP | 2001 218733 A | 8/2011 |
| WO | WO 2009/029106 A1 | 3/2009 |
| WO | WP 2009/100106 A1 | 8/2009 |

OTHER PUBLICATIONS

Patent Examination Report No. 1 dated Dec. 21, 2012 for Australian Application No. 2010241834.
International Search Report issued in corresponding application PCT/US2015/051984, dated Nov. 30, 2015, pp. 1-3.

* cited by examiner

ENDOSCOPE MOUNTABLE VISUALIZATION DEVICE QUICK-CONNECT/RELEASE HANDLE ATTACHMENT MECHANISM

CROSS-REFERENCE TO RELATED APPLICATIONS

This application claims priority under 35 U.S.C. §§ 120-121 to U.S. application Ser. No. 14/863,732 and to U.S. provisional application Ser. No. 62/056,904, filed Sep. 29, 2014, each of which is incorporated by reference herein in its entirety.

TECHNICAL FIELD

Embodiments disclosed herein generally relate to medical endoscopy devices. More particularly the embodiments relate to a connection mechanism for a steerable catheter including a distal visualization element.

BACKGROUND

Cholangioscopy is a minimally invasive endoscopic method used both for direct visual diagnostic evaluation of and for therapeutic intervention in the bile ducts. Peroral cholangioscopy overcomes some of the limitations of endoscopic retrograde cholangiopancreatography (ERCP) alone, although the procedures may be done together. Pancreatoscopy is the direct visual evaluation of the pancreatic ducts.

Although it has been in limited use since the 1950s, cholangioscopy has recently become more practically feasible, due in part to advances in endoscopic technique, scope design/materials, and functionality. However, cholangioscopes (and related smaller endoscopes that are dimensioned to be operated through a working channel of standard gastric endoscope, duodenoscope or the like, as well as within the bile ducts of a human patient, referred to as "miniscopes" or "baby scopes" where the larger scope is a "mother scope") have several limitations. For example, certain models require two endoscopists (see, e.g., FIG. 1A, where a first endoscopist 102 operates the "mother scope" 110, and a second endoscopist 104 operates the "baby scope" 140). This significantly increases the cost of procedures and complicates the logistics in smaller operating suites.

As shown in FIG. 1B, other miniscope models, although designed for use by a single endoscopist, may have control surfaces 142 for steering/manipulating and operating the miniscope 140 disposed offset at a significant distance from the control surfaces 112 of the larger endoscope 110 through which the miniscope 140 is situated. Those of skill in the art will appreciate that this can be uncomfortable for the user/endoscopist, as the position of the miniscope controls 142 is a significant distance away from the mechanical center of stability of the two-scope system, which center of stability is necessarily created by the endoscopist's left hand.

As a consequence, with this type of miniscope, forces impacting upon the system due to manipulation of the miniscope controls (and port features) create significant torsional moments about the center of stability at the endoscopist's left hand. This is due to the long moment arm through which these forces act. These torsional moments must be resisted by the left hand of the endoscopist, and can create difficulty with control as well as operator fatigue. In addition, the strap-mounting structure 143 used for mounting such a miniscope 140 below the mother scope's accessory channel 114 leaves a prominent gap 141a between the two endoscopes' control surfaces, as well a prominent cross-hatched gap region 141b between the two endoscopes bodies, which (due in part to the relative body lengths compared to the length of attachment region) can create an unstable coupling, such that—under the typical forces of manipulation—this type of miniscope may rock, shift, slip downwards, or pivot about the primary axis of the larger "mother scope" (e.g., duodenoscope). These movements can create additional difficulty, stress, and fatigue for the endoscopist, which can have a negative impact.

Cholangioscopy is known to be an effective diagnostic and therapeutic tool, and there is a need for providing a miniscope that addresses needs in the existing art while providing technology that is diagnostically effective, therapeutically effective, and cost-effective. It may be desirable to provide a miniscope, configured for use in cholangioscopy or other dual-endoscope procedures that provides a secure, rigid mounting of two scopes together, with control surfaces provided and located to promote ease of efficient operation.

BRIEF SUMMARY

In one aspect, embodiments disclosed herein may include a dual medical endoscope system including a smaller scope attached to and extending partially through a larger scope, with methods for assembling, disassembling, and using the same for medical observational, diagnostic, and/or therapeutic methods.

In one aspect, embodiments of a medical endoscope disclosed herein may include an elongate, manipulable shaft including a distal-end visualization element; and a handle body comprising at least one control surface for manipulating a distal region of the shaft; where the handle body includes a passage through which a length of the shaft is passable; and where the handle body includes a connection structure configured for securely and removably mounting the handle to a channel of a second endoscope in a manner axially aligning the passage with the channel to provide a path of communication for the shaft.

In certain aspects embodiments may include a dual medical endoscope system, with a first medical endoscope and a second medical endoscope, where the first medical endoscope includes an accessory channel with a proximal mounting port providing access thereto, and where the second medical endoscope includes a handle body that is securely and removably attached to the proximal mounting port.

In other aspects, embodiments may include a method for performing a dual-endoscope procedure, where the method includes steps of: providing a first, larger, endoscope and a second, smaller, endoscope; where the larger endoscope includes an accessory channel with proximal engagement structure providing direct access to the channel, where a distal shaft of the second endoscope is sized for passage through the channel, and where the second endoscope includes a connection structure configured for securely and removably mounting a handle of the second endoscope directly to the proximal engagement structure of the first endoscope's accessory channel; and directing a distal shaft of the first endoscope to a target region; and directing the distal shaft of the second endoscope through the channel of the first endoscope.

Certain embodiments, in another aspect, may relate to a medical endoscope with an elongate, manipulable shaft including a distal-end visualization element; and a handle body comprising at least one control surface for manipulating a distal region of the shaft; where the handle body includes a structure through which a length of the shaft is passable; and where the handle body includes a connection structure configured for securely and removably mounting the handle to a channel of a second endoscope in a manner axially aligning the passage with the channel to provide a path of communication for the shaft.

DETAILED DESCRIPTION

Figure 1A:
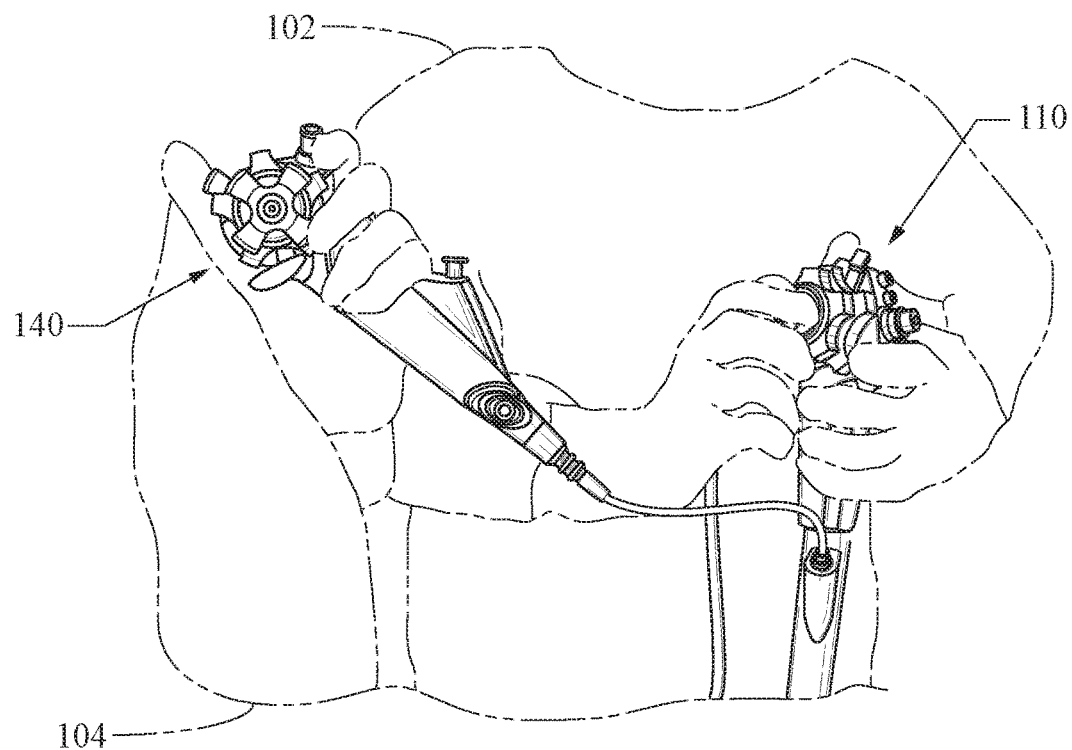
FIGS. 1A and 1B show examples of known dual-endoscope configurations.

Various embodiments are described below with reference to the drawings in which like elements generally are referred to by like numerals, except where otherwise noted. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The terms "about," "generally," and "essentially" when used with reference to any volume, dimension, proportion, or other quantitative value are intended to communicate a definite and identifiable value within the standard parameters that would be understood by one of skill in the art (equivalent to a medical device engineer with experience in the field of endoscope devices), and should be interpreted to include at least any legal equivalents, minor but functionally-insignificant variants, and including at least mathematically significant figures.

An in-vivo visualization device configured for viewing and/or performing diagnostic and therapeutic procedures within the human body, such as in the biliary tree, may include a steerable catheter shaft with a distal visualization modality (e.g., a complementary metal oxide silicon (CMOS) sensor). The device may be configured as an endoscope in the manner of a so-called miniscope or "baby scope" operable through the accessory channel of a larger "mother scope" (e.g., a duodenoscope). In particular, the device may be configured to be securely, rigidly, and removably attached directly to the proximal mounting port of an accessory channel of the mother scope with the steerable shaft of the device disposed through that channel. By "rigidly," the present disclosure refers to a substantially solid and inflexible connection where the "baby scope" remains in a substantially fixed orientation relative to the "mother scope" without flexing or otherwise moving relative thereto unless the connection is released, (e.g., specifically in contrast with known devices that allow flexure between the handle bodies of two attached scopes). As such, in one aspect, embodiments of the present disclosure may include a dual endoscope system. As used herein, the phrase "configured to" (including "configured for") is not aspirational, nor does it merely indicate a statement of intended use; rather, "configured to" describes specific structural limitations as expressly disclosed (including their legal equivalents) which will be understood by those of skill in the art as providing an effective structure and mechanism dictated by and particularly suited for the function described. In other words, the phrase "configured for" means that the structure configured for a given function and/or structural interface is effective for doing that as interpreted within the boundaries of the present specification and its legal equivalents.

In one aspect, presently disclosed embodiments address the need in the art for a dual endoscope system to perform cholangioscopy and/or other procedures for diagnostic and therapeutic purposes. In particular, the need is addressed for such a system that locates the control surfaces of a primary endoscope and the control surfaces of a secondary endoscope in close proximity, with the secondary endoscope securely, rigidly, and removably attached directly to the proximal mounting port of an accessory channel of the primary endoscope. The attachment provides for operation of a manipulable shaft of the secondary endoscope through the accessory channel of the primary endoscope.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used herein in the common usage sense where they refer respectively to a handle/doctor-end of a device or related object and a tool/patient-end of a device or related object. The term "Luer-type" is used to refer to (and includes) Luer taper or similar fluid-tight fitting engagement interfaces that are engageable to form a tight connection based upon the angles of interfacing surfaces, well-known in the art, and includes engagement structures known as "Luer lock" connections. Luer-type connections, threaded connections, bayonet-style connections, frictional slide-clamps, snap-fit, set-screws, and other connection interfaces useful in attaching two generally tubular structures are so well known in the art that the present disclosure does not belabor all the variants and combinations thereof, although each of them (alone or in combination with other connection means—whether listed or not) may be used within the presently disclosed embodiments. Cholangioscopy is a specific intraductal endoscopic technique. The structures and methods disclosed herein may be useful in a variety of diagnostic and therapeutic endoscopy procedures, and may particularly be useful during cholangioscopy, whether conducted alone or in conjunction with ERCP (endoscopic retrograde cholangiopancreatography). The intracorporeal aspects of dual-scope procedures (e.g., endoscopic retrograde cholangiopancreatography, endoscopic retrograde cholangiography, cholangioscopy, and others) are very well characterized in the medical endoscopy art, such that reference to such procedures herein will be fully comprehended by those of skill in the art given the focus of the present disclosure upon extracorporeal connection structures of an endoscope (described and claimed herein) to a second endoscope (which may be a standard endoscope not claimed herein, or part of a system incorporated in the presently disclosed and claimed subject matter).

Figure 2A:
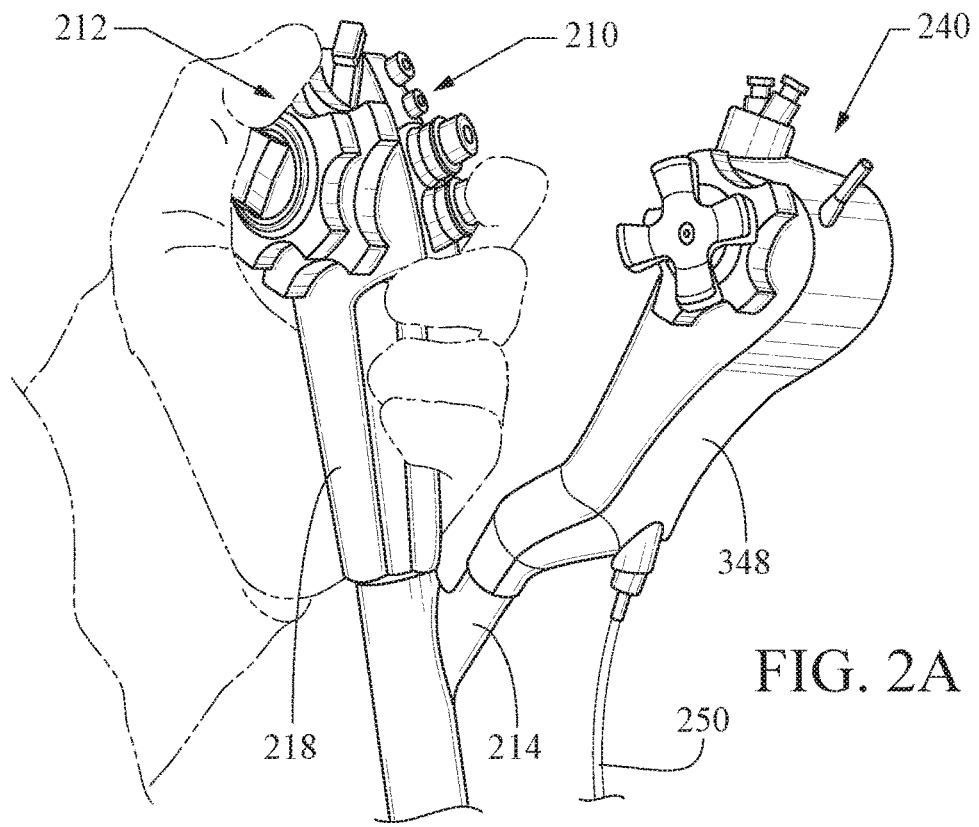
FIGS. 2A and 2B show two perspective views of a larger endoscope and a smaller endoscope (miniscope).
Figure 2B:
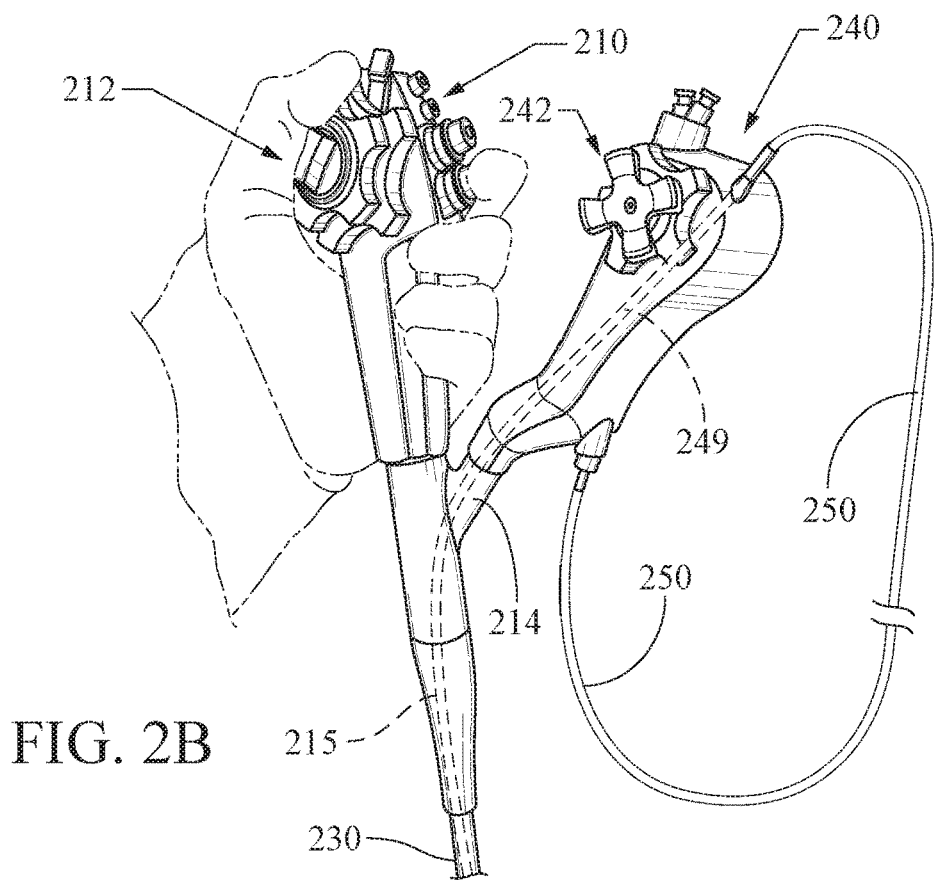
Figure 4:
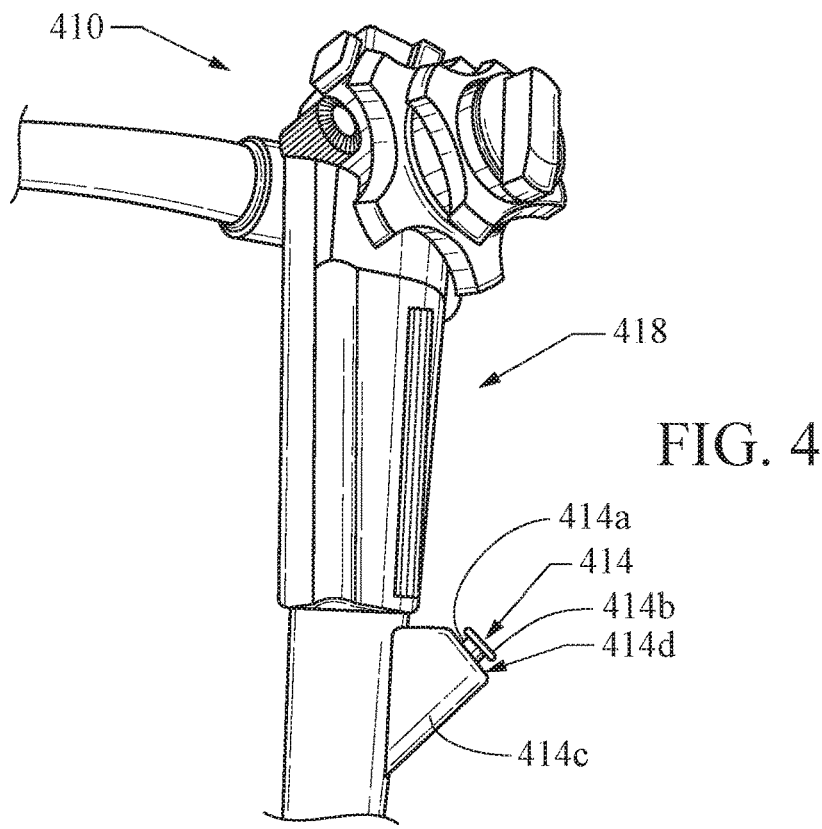
FIGS. 4 and 5 show two examples of endoscope accessory port configurations.
Figure 5:
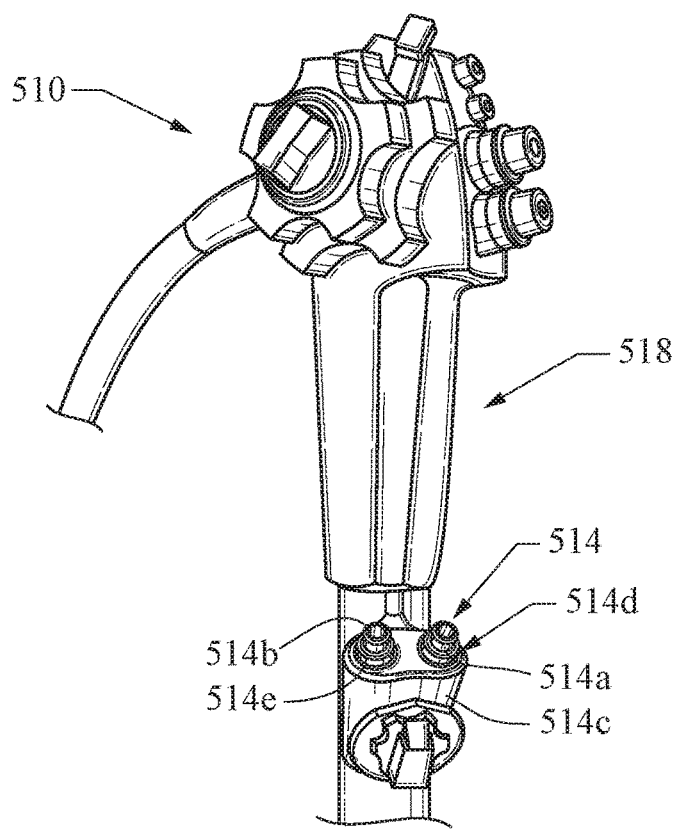

To provide context, a medical endoscope system is described with reference to FIGS. 2A and 2B, which show, respectively, two perspective views of a larger first endoscope 210 and a smaller second endoscope (miniscope) 240. The handle body 248 of the miniscope 240 is securely and removably attached directly to the accessory port portion 214 of the first endoscope 210. FIGS. 4-5 show exemplary accessory port structures 414 and 514 of different larger endoscopes. Those of skill in the art will appreciate, with reference to the present disclosure (including, for example, FIGS. 6A-6E) and the state of the art, that the miniscope 240 may be directly, securely, rigidly, and removably and adjustably attached to different accessory port configurations as those configurations may vary across different types (e.g., by medical application and/or by manufacturer) of larger endoscopes. The term "adjustably" in this context refers to the adjustability of the miniscope's connection with respect to axial rotation of the miniscope around the long axis of its handle and/or the long axis of its connection with a larger scope (which, in many embodiments, may be defined by the miniscope's shaft body).

A medical endoscope (including so-called "miniscope" such as cholangioscope, or other small-scale endoscope) should be understood as useful with embodiments of the presently described connection mechanisms and systems. This includes at least those devices described in U.S. Pat. App. Pub. No. 2015/0057537 to Dillon et al., which is incorporated herein by reference in its entirety.

The first endoscope 210 includes a handle body 218 with proximal/upper-end control surfaces 212 for operation (e.g., manipulation of the shaft and control of visualization elements). In the illustrated embodiment, the miniscope 240 also includes control surfaces 242 for operation (e.g., manipulation of the shaft and control of visualization elements). In certain embodiments, at least one control surface of the smaller endoscope 240 is configured substantially similarly to at least one control surface of the first endoscope 210. It may be preferable that all control surfaces are configured substantially similarly or even exactly the same so that an endoscopist can readily operate both scopes with the same relative motions generating the same relative response of the distal shaft and other elements. The proximity and similar orientation of both scopes' control surfaces 212, 242 will promote efficiency and ease of operation.

The miniscope 240 includes an elongate shaft 250 that preferably is manipulable in at least two, and preferably at least three, dimensions and that includes at or near its distal end a visualization element such as, for example, a CMOS sensor. Specific elements of the control surfaces, shaft manipulation/steering means, shaft lumens, and other features may be configured similarly to other endoscopy devices, or may have unique, novel configurations not described herein. The shaft 250 extends from a lower/distal end of the miniscope handle body 248 and loops back around to pass via a miniscope handle passage 249 through the accessory port (not shown) into the accessory channel 215 of the larger scope 210. The miniscope shaft 250 is dimensioned so that it will extend through the accessory channel 215 and out of a distal end of the first endoscope shaft 230, and preferably be freely slidable therethrough to allow longitudinal manipulation by a user in the manner desired (e.g., for cholangioscopy).

Figure 3:
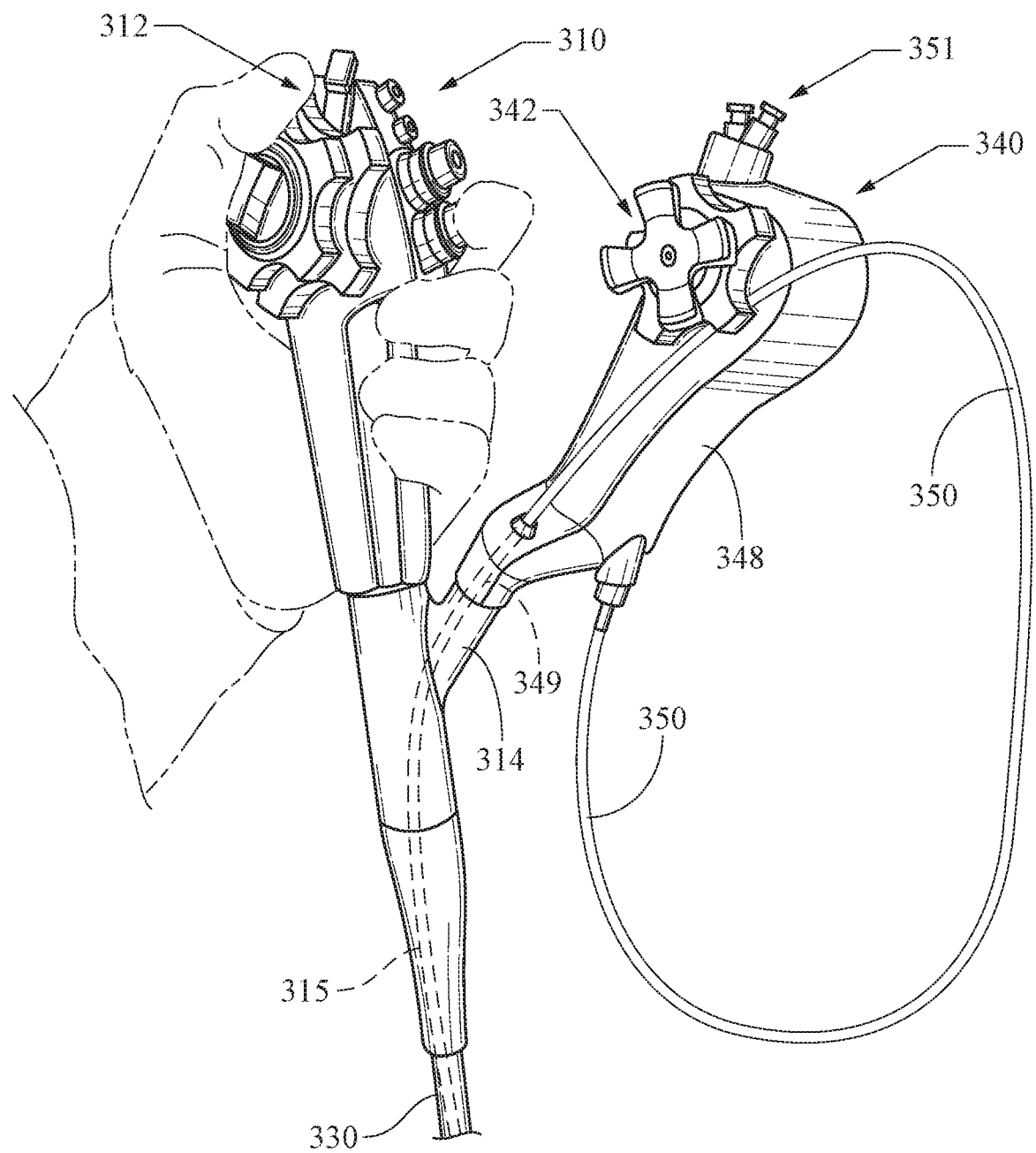
FIGS. 3 and 3A each shows a dual-endoscope assembly where each smaller endoscope embodiment includes an offset handle portion relative to a shaft passage.

In another embodiment of a medical endoscope system, shown in FIG. 3, a miniscope 340 may be provided with a handle body 348 providing a handle passage 349 that extends through only a minor length (less than about one-half the length) of the handle body 348. In this embodiment, a portion of the handle body 348 is axially offset relative to the handle passage 349 and the connection structure, such that the passage extends through less than a majority length of the handle body 348.

As shown in FIG. 3, a larger first endoscope 310 and a smaller second endoscope (miniscope) 340 are shown. The handle body 348 of the miniscope 340 is securely, removably, and adjustably attached directly to the accessory port portion 314 of the first endoscope 310. The first endoscope 310 includes control surfaces 312 for operation (e.g., manipulation of the shaft and control of visualization elements). In the illustrated embodiment, the miniscope 340 also includes control surfaces 342 for operation that preferably are configured substantially similarly to at least one control surface of the first endoscope 310.

Figure 1B:
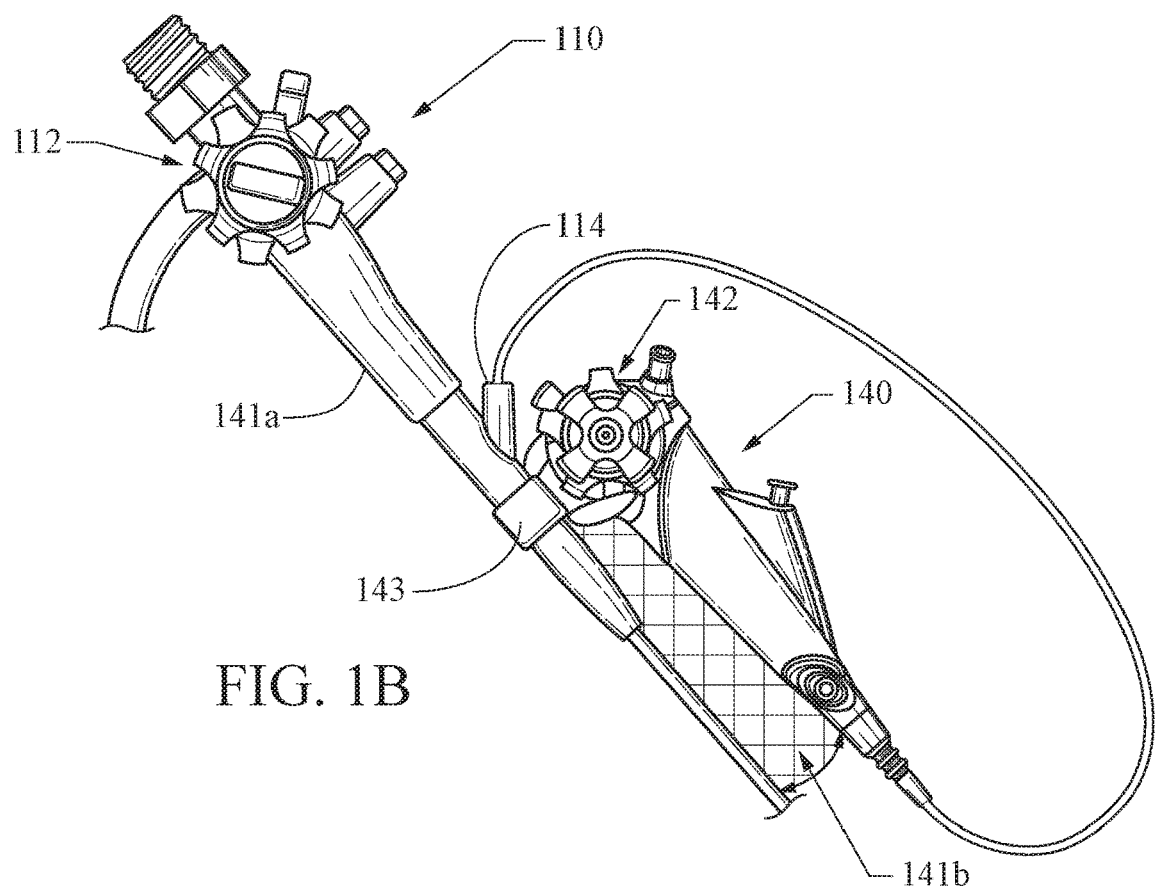

The miniscope 340 includes an elongate catheter shaft 350 that preferably is manipulable in at least two or (more preferably) three dimensions and that—in this and other embodiments—may include one or more other channels/lumens (e.g., for passage therethrough of guidewire(s), therapeutic and/or diagnostic tools, fluids (e.g., radiopaque contrast, flushing fluid), and/or other materials), accessible through one or more ports 351 on the proximal region of the handle body 348. The miniscope 340 may also include at or near its distal end a visualization element (not shown) such as, for example, a CMOS sensor. Specific elements of the control surfaces, shaft manipulation/steering means, shaft lumens, and other features may be configured similarly to other endoscopy devices, or may have unique, novel configurations not described herein. The shaft 350 extends from a lower/distal end of the miniscope handle body 348 and loops back around to pass via the offset miniscope handle passage 349 through the accessory port 314 into the accessory channel 315 of the larger scope 310. The miniscope shaft 350 is dimensioned so that it will extend through the accessory channel 315 and out of a distal end of the first endoscope shaft 330, and preferably will be freely slidable therethrough to allow longitudinal manipulation by a user in the manner desired. In this embodiment, the miniscope shaft 350 will have less frictional contact with the handle body than may be present in other embodiments. This will also allow a user readily to longitudinally manipulate the miniscope shaft 350 from a familiar position/orientation of gripping and manipulating the miniscope shaft (e.g., relative to prior devices shown in FIGS. 1A-1B).

Figure 3A:
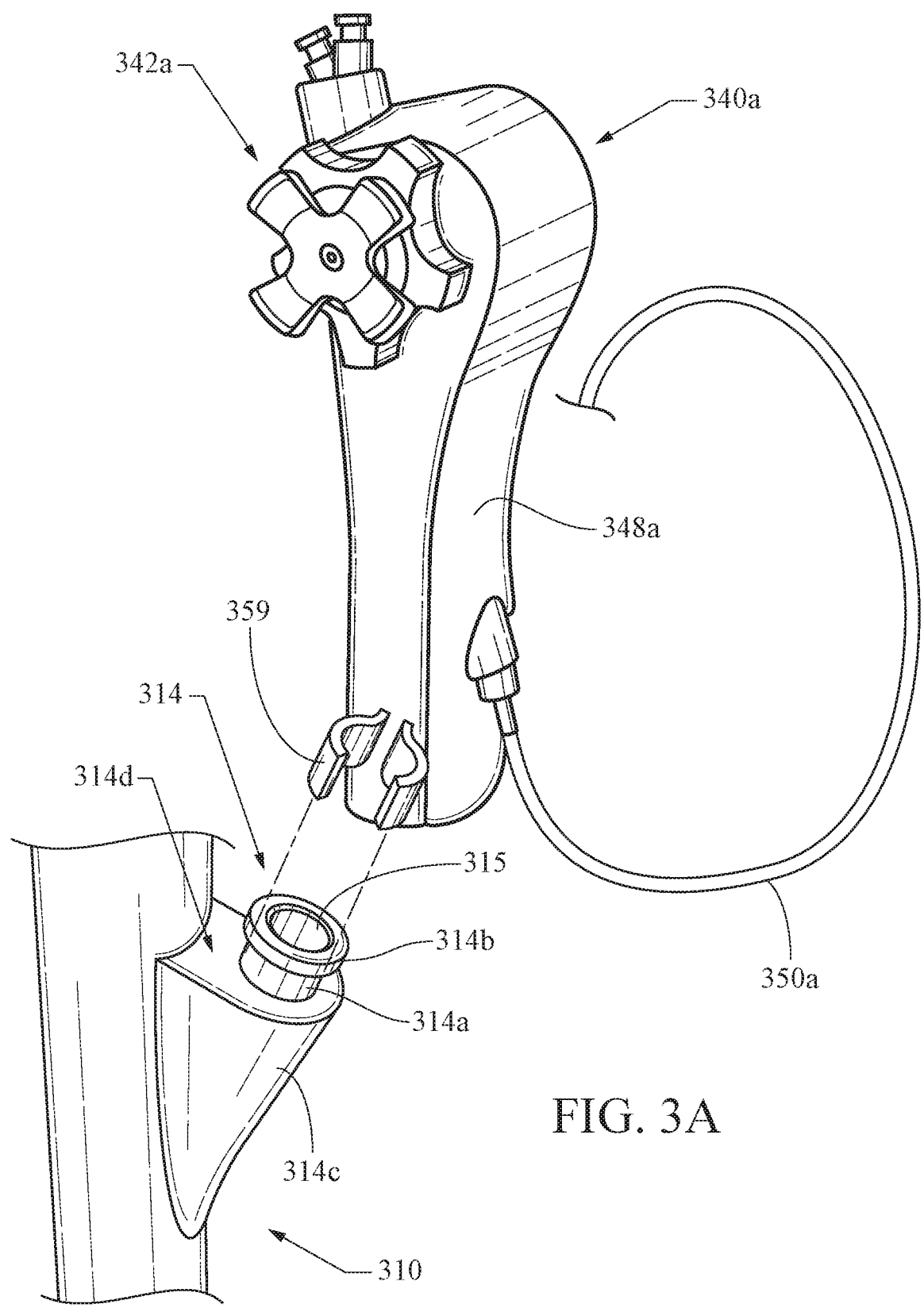

In FIG. 3A, the larger first endoscope 310 is shown with a smaller second endoscope (miniscope) 340a. The handle body 348a of the miniscope 340a is securely, removably, and adjustably attachable directly to the accessory port portion 314 of the first endoscope 310. In the illustrated embodiment, the miniscope 340a also includes control surfaces 342a for operation that preferably are configured substantially similarly to at least one control surface of the first endoscope 310.

The miniscope 340a includes an elongate catheter shaft 350a that preferably is manipulable in at least two or (more preferably) three dimensions. The shaft 350a is shown truncated, but—in this and other embodiments—may include one or more other channels/lumens (e.g., for passage therethrough of guidewire(s), therapeutic and/or diagnostic tools, fluids (e.g., radiopaque contrast, flushing fluid), and/or other materials), accessible through one or more ports on the proximal region of the handle body 348a. The miniscope 340a may also include at or near its distal end a visualization element (not shown) such as, for example, a CMOS sensor. Specific elements of the control surfaces, shaft manipulation/steering means, shaft lumens, and other features may be configured similarly to other endoscopy devices, or may have unique, novel configurations not described herein. The shaft 350a extends from a lower/distal end of the miniscope handle body 348a and loops back around to pass alongside the offset miniscope handle body 348a through the accessory port 314 into the accessory channel 315 of the larger scope 310. The term "offset" refers to the alignment of the long axis of the miniscope handle body 348 relative to the long axis of the larger scope's accessory port 314 when the clip is engaged thereabout.

The miniscope shaft 350a is dimensioned so that it will extend through the accessory channel 315 and out of a distal end of the first endoscope shaft, and preferably will be freely slidable therethrough to allow longitudinal manipulation by a user in the manner desired. In this embodiment, the miniscope shaft 350a will have less frictional contact with the handle body than may be present in other embodiments. This will also readily allow a user to longitudinally manipulate the miniscope shaft 350a from a familiar position/orientation of gripping and manipulating the miniscope shaft (e.g., relative to prior devices shown in FIGS. 1A-1B).

The larger endoscope's accessory port 314 extends from a side of its lower/distal handle portion. It includes a cylindrically tubular metal body 314a with a protruding annular lip 314b. A base 314c of the port includes a flat surface 314d generally perpendicular to the central long axis of the tubular port body 314a. A connection clip assembly 359 of the miniscope handle 348a is configured to engage around the tubular port body 314a between the annular lip 314b and the flat surface 314d to hold the miniscope handle rigidly, adjustably, securely, and removably to the larger scope handle in a manner that aligns the passage of the miniscope with the port and the accessory channel 315 to permit transit therethrough of the miniscope shaft 350a.

Two examples of accessory port structures of larger ("mother") endoscopes are shown in FIGS. 4-5. Those of skill in the art will appreciate that different types of endoscopes (e.g., duodenoscopes, bronchoscopes, colonoscopes, etc.) may have different accessory channel port configurations, which may vary by the scopes' makers and/or uses. Different embodiments of the present disclosure may include miniscopes, handles, and connection structures configured for connection with any of those accessory port designs, and practiced within the scope of the present disclosure and claims.

FIG. 4 shows one example of a handle 418 of a duodenoscope 410. The accessory port 414 extends from a side of the lower/distal handle portion. It includes a cylindrically tubular metal body 414a with a protruding annular lip 414b. A base 414c of the port includes a flat surface 414d generally perpendicular to the central long axis of the tubular port body 414a. For this type of port structure, a connection portion of a miniscope of the present disclosure may include structure that engages the annular lip 414b and the flat surface 414d to hold the miniscope handle rigidly, securely, and removably to the larger scope handle 418 in a manner that aligns the passage of the miniscope with the port and the accessory channel to permit transit therethrough of the miniscope shaft. In one aspect of each of the endoscopes disclosed herein, a miniscope handle portion may engage into the inner diameter of (and/or around the outside diameter of) the tubular port body 414a (in the manner shown in FIG. 6E by way of example of handle body extension 662 into the inner diameter of the larger scope's working channel, or in another manner).

FIG. 5 shows an example of a handle 518 of a colonoscope 510. The accessory ports 514 extend from a side of the lower/distal handle portion. They each include a cylindrically tubular metal body 514a with a protruding annular lip 514b and a protruding annular ring 514e near where the exposed metal tubular body meets the base 514c of the port at a flat surface 514d generally perpendicular to the central long axis of the tubular port body 514a. For this type of port structure, a connection portion of a miniscope of the present disclosure may include structure that engages the flat surface 514d and one or both of the annular lip 514b and the annular ring 514e to hold the miniscope handle rigidly, securely, and removably to the larger scope handle 518 in a manner that aligns the passage of the miniscope with the port and an accessory channel to permit transit therethrough of the miniscope shaft. In some embodiments, the annular lip may be configured as a Luer type connector element or a threaded connector element for securing items to the port in a manner that preferably will—like the other connections described herein—maintain a seal (e.g., to maintain patient insufflation, prevent escape/leakage of patient body fluids, etc.).

Turning now to the embodiments of the particular invention, each may incorporate some or all of the features described above. Any elements from each of the earlier embodiments discussed above that are not expressly discussed or numbered are incorporated and included as if reprinted here.

FIGS. 6A-6E show an embodiment of a connection structure of a miniscope configured for securely and removably mounting the miniscope handle to an accessory port channel of a second endoscope in a manner axially aligning the miniscope shaft passage with the second endoscope's accessory channel to provide a path of communication for the miniscope shaft therethrough. Those of skill in the art will appreciate that the structures described and illustrated with reference to this embodiment provide for a quick-connect/release mechanism that is configured to (i.e., effectively will, as herein defined) securely, rigidly, and removably couple a first endoscope to a second endoscope, where a very few small simple movements by a user will effect connection with or release from, as needed, of the first endoscope and second endoscope.

Figure 6A:
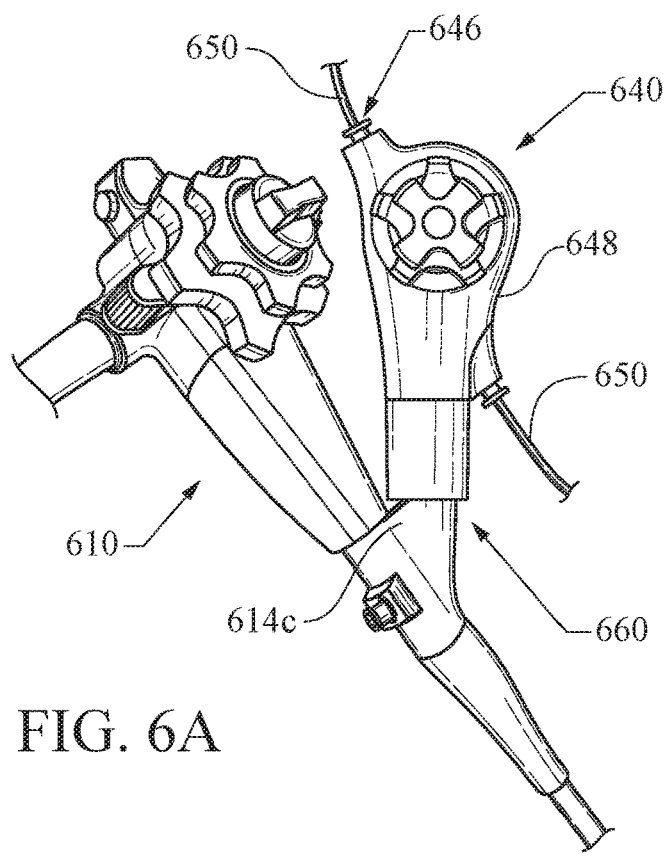
FIGS. 6A-6E show an embodiment of the present quick-connect/release connection structure.
Figure 6B:
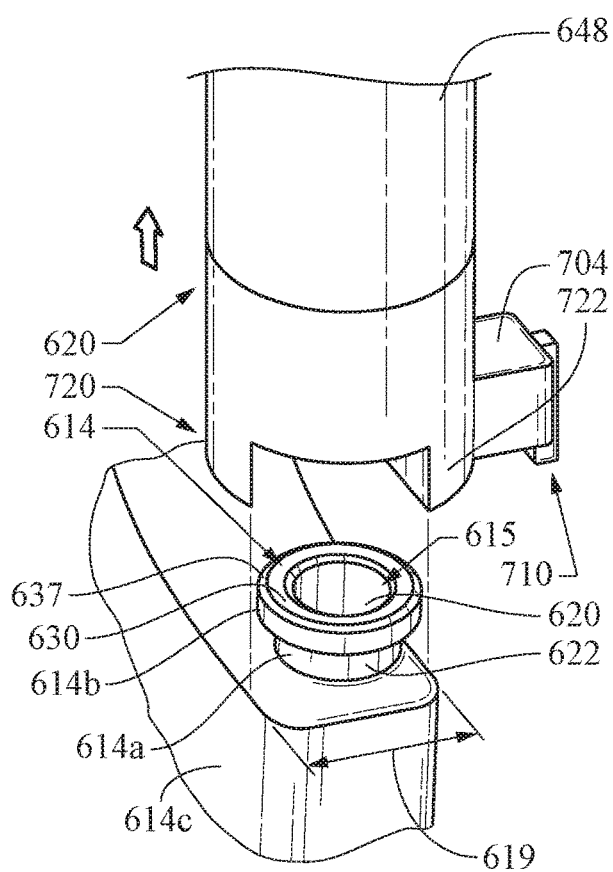

FIG. 6A shows an embodiment of a connection structure/endoscope locking mechanism 660 as part of a first endoscope, or miniscope 640 that is securely and rigidly, but removably and adjustably, attached to a second, larger endoscope 610. Of course, the use of the terms first endoscope can identify the endoscope 610 and the second endoscope can identify the miniscope 640; thus, it rather is merely a term of convention. FIGS. 6A-6E show the structure and function of the first connection structure 660.

Figure 6C:
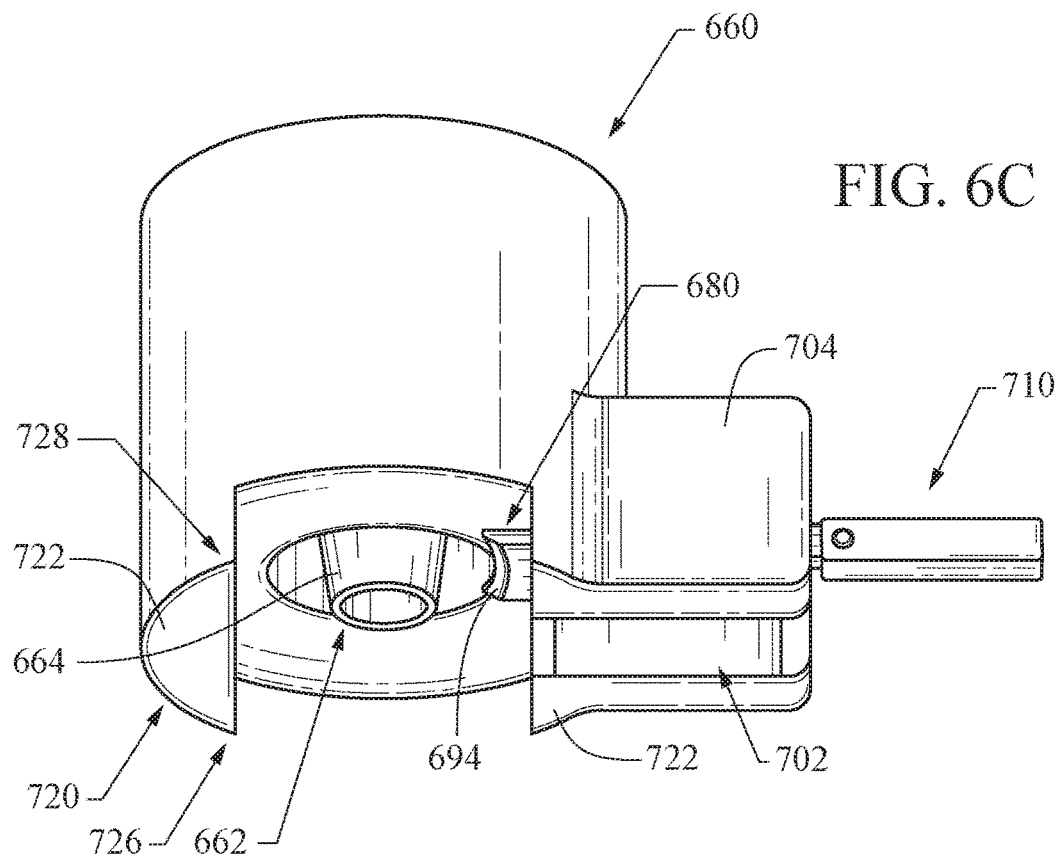
Figure 6D:
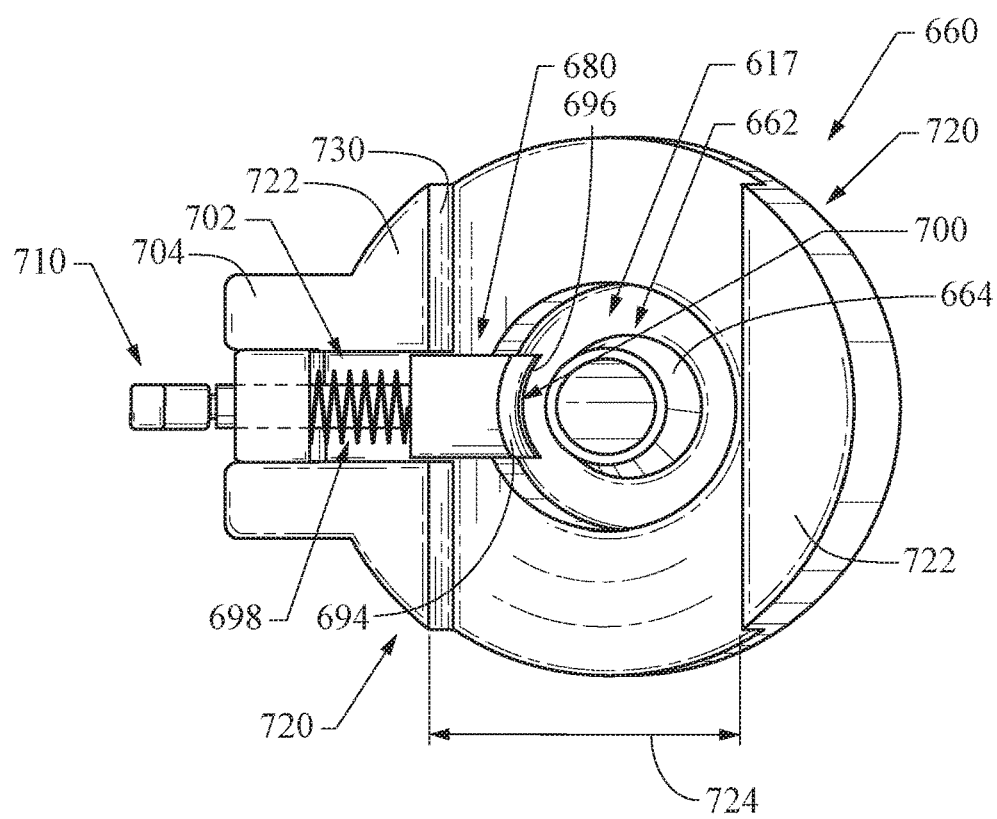
Figure 6E:
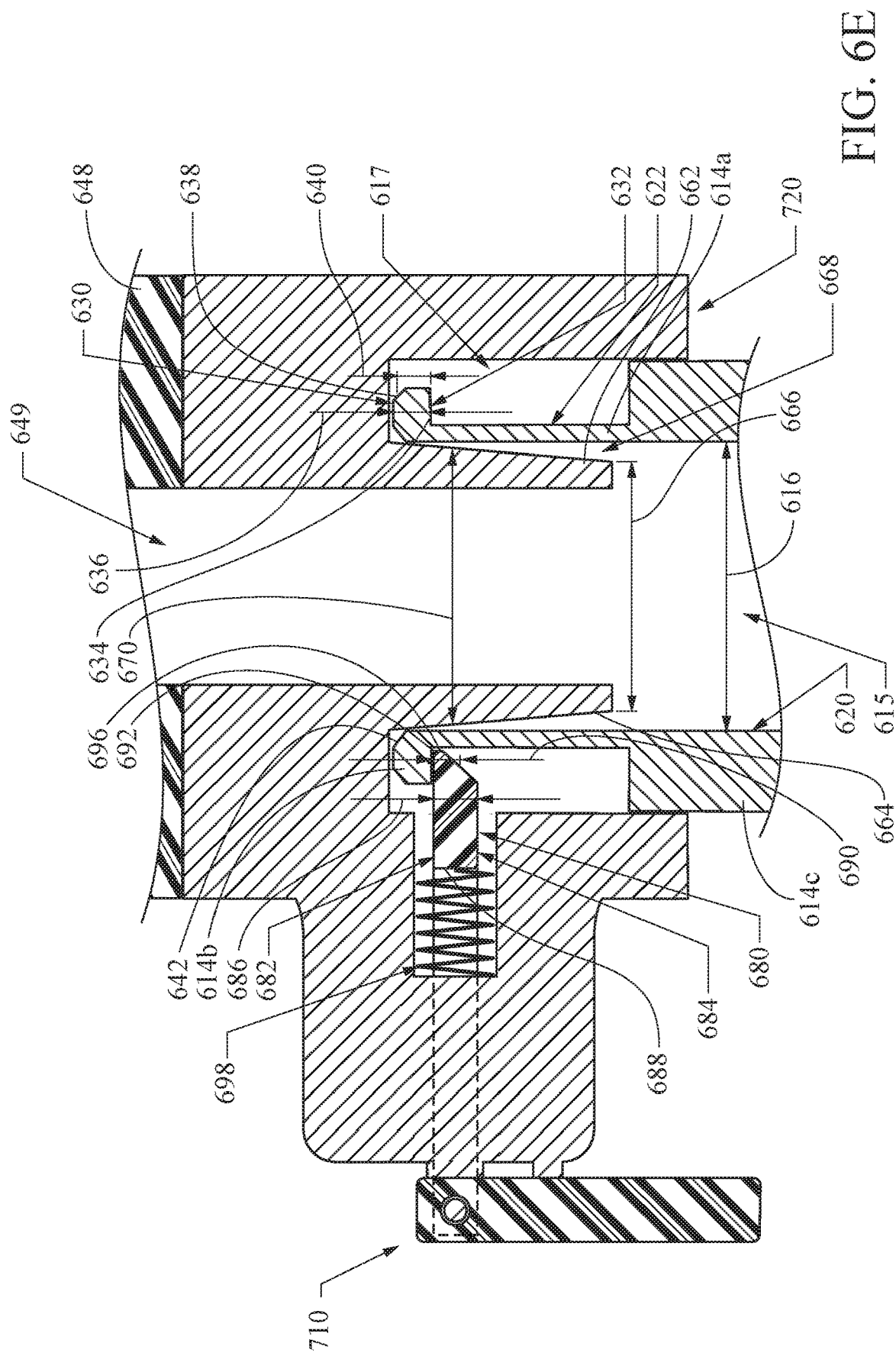

As may be seen in FIGS. 6A and 6E, when the connection structure 660 is aligned with and/or engaged to the port 614, the miniscope handle passage 649 (FIG. 6E) is aligned with and secured to the accessory channel 615 of the larger scope 610. This will allow operation of the miniscope catheter shaft body 650 into miniscope port 646, through the miniscope handle body 648, then into and through the accessory channel 615 of the larger scope.

In FIGS. 6A-6E, the second endoscope 610 includes the mounting port 614. The mounting port 614, in turn, includes a tubular element 614a, an annular lip 614b, and a base 614c. The tubular element 614a extends away from the base 614c. An inner surface 620 of the tubular element 614a defines an accessory channel 615 that has a channel diameter 616 as best illustrated in FIG. 6E. The tubular element 614a also includes an outer surface 622 spaced apart from the inner surface 620.

As best illustrated in FIG. 6E, the annular lip 614b extends radially away from the tubular element 614a. The annular lip 614b includes an upper surface 630 and a lower surface 632 spaced apart from the upper surface 630. Between the upper surface 630 and the lower surface at a first location 634 exists a first height 636. At a second location 638 radially spaced apart and away from the tubular element 614a relative to the first location 634, there exists a second height 640 between the upper surface 630 and the lower surface 632. In some embodiments, the first height 636 and the second height 640 are the same within manufacturing tolerances. In other embodiments, the second height 640 is less than the first height 636 so as to form a tapered surface 637 (FIG. 6B) downward or towards the base 614c. Optionally, a similar tapered surface 642 may be formed proximate the upper surface 630 in a direction radially towards the tubular element 614a.

The connection structure 660 is configured to couple a handle body 648 to the second endoscope 610 at the mounting port 614 so as to axially align the accessory passage 649 with the accessory channel 615. The connection structure 660 includes a recessed portion configured to receive at least one of a portion of the tubular element 614a and a portion of the base 614c of the mounting port 614, as illustrated in FIGS. 6D and 6E.

As best illustrated in FIGS. 6C-6E, an extension 662 is configured to be inserted within the accessory channel 615. The extension 662 includes an outer surface 664 configured to provide a sealable connection with at least one of the annular lip 614b and the inner surface 620 of the tubular element 614a. The outer surface 664 of the extension 662 has a first diameter 666 at a distal end 668 of the extension 662 and a second diameter 670 at a location on the extension 662 proximal to the first diameter 666. The first diameter 666 is smaller or less than the second diameter 670. In other words, there exists at least one diameter located in a proximal (upward in FIG. 6E) direction away from the first diameter 666 that is larger than the first diameter 666. In some embodiments, the outer surface 664 may form a tapered surface, a ridged surface, a curved surface, or another shape of surface.

At least one of the first diameter 666 and the second diameter 670 of the extension 662 is substantially the same as the channel diameter 616. By substantially the same, it is meant that the diameters are within plus-or-minus 10% of the length of each other and, more preferably within plus-or-minus 5% or less. In some embodiments, at least one of the first diameter 666 and the second diameter 670 of the extension 662 is such that it provides an interference fit between the outer surface 664 of the extension 662 and the inner surface 620 of the tubular element 614a. Typically, the first diameter 666 would be smaller than the channel diameter 616.

The change in diameter of the outer surface 664 helps to ease the insertion of the extension 662 into the accessory channel 615 in the first instance. As the extension 662 is inserted further, the diameter of the outer surface 664 increases (is greater) in at least one location so as to provide a sealable or sealing connection with the inner surface 620 of the tubular element 614a. Further, the outer surface 664 of the extension 662, by virtue of contacting at least a portion of the inner surface 620 of the tubular element 614a, helps to stabilize and rigidly hold or couple the first endoscope 640 to the second endoscope 610.

The connection structure 660 also includes a locking mechanism 680 configured to engage the outer surface 622 of the tubular element 614a. The locking mechanism 680 includes an upper surface 682 and a lower surface 684 spaced apart from the upper surface 682 so as to provide a first height 686 between the upper surface 682 and the lower surface 684 at a first location 688 on the locking mechanism 680. There also is at least a second height 690 between the upper surface 682 and the lower surface 684 at a second location 692 on the locking mechanism 680 laterally spaced apart and towards the tubular element 614a relative to the first location 688. In some embodiments, the first height 686 and the second height 690 are the same within manufacturing tolerances. In other embodiments, the second height 690 is less than the first height 686 so as to form a tapered surface 694, best illustrated in FIGS. 6C and 6D, that tapers upward or towards the handle body 648.

The tapered surface 694 of the locking mechanism 680 interacts with the annular lip 614b and, in particular, the tapered surface 637 of the annular lip 614b when the first endoscope 640 is coupled to the second endoscope 610. The tapered surfaces 637 and 694 ease the insertion of the extension 662 into the accessory channel 615 by reducing the force necessary to urge the locking mechanism 680 laterally away from the annular lip 614b during the coupling process.

Once an engagement surface 696 (FIGS. 6D and 6E) passes the annular lip 614b during the coupling process, a biasing mechanism 698 urges the locking mechanism 680 laterally towards the outer surface 622 of the tubular element 614a. In some embodiments, the biasing mechanism 698 urges the engagement surface 696 to engage or otherwise come into contact with the outer surface 622 of the tubular element 614a, while in other embodiments the engagement surface 696 does not contact the outer surface 622.

At least a portion 700 (FIG. 6D) of the engagement surface 698 has a radius of curvature substantially the same as a radius of curvature of the outer surface 622 of the tubular element 614a. In addition, once in the locked position (FIG. 6E), the upper surface 682 of the locking mechanism 680 lies below and, in some embodiments, in contact with, the lower surface 632 of the annular lip 614b. The locking mechanism 680 thus engages at least one of the annular lip 614b and the outer surface 622 of the tubular element 614a to help stabilize and rigidly hold or couple the first endoscope 640 to the second endoscope 610. As the engagement surface 696 moves towards and comes into contact with the tubular element 614a and/or the annular lip 614b, the user may here an audible click and/or feel the locking mechanism 680 engage with the tubular element 614a and/or the annular lip 614b. Such indicators—the sound and sensation/feeling of engagement—ensure the user that positive locking between the first endoscope 640 and the second endoscope 610 has occurred.

The biasing mechanism 698 typically is a spring of any known type, although other structures that provide a similar force are suitable, such as rubber elements and the like.

The biasing mechanism 698 and, optionally, a portion of the locking mechanism 680, are disposed within a recess or channel 702 within a housing 704 of the connection structure 660 as best illustrated in FIG. 6D.

The connection structure 660 also includes a release mechanism 710 coupled to at least one of the locking mechanism 680 and the biasing mechanism 698. Typically, the release mechanism 710 is a lever pivotably coupled to the biasing mechanism 698, which in turn is coupled to the locking mechanism 680. The release mechanism 710 is configured to disengage the locking mechanism 680 from the outer surface 622 of the tubular element 614*a* by drawing the locking mechanism 680 radially away from the outer surface 622 of the tubular element 614*a*.

As best illustrated in FIGS. 6C and 6D, the connection structure 660 further includes at least another connection structure 720 configured to engage the base 614*c* of the mounting port 614. Typically, the shape of the connection structure is such that a portion of the connection structure 660 forms at least one leg element 722 that extends distally away from the handle body 648 of the first endoscope 640. While the legs or leg elements 722 are formed integrally with the connection structure 660 in the illustrated embodiments, it is understood that the legs 722 alternatively could be separate structures coupled to the connection structure 660.

As illustrated in FIG. 6D, at least two legs 722 have a distance 724 between each of the legs 722 that is substantially the same as a distance 619 (FIG. 6B) spanning the base 614*c* of the mounting port 614. By substantially the same, it is meant that the distances 619 and 724 are within plus-or-minus 10% of the length of each other and, more preferably within plus-or-minus 5% or less. Alternatively, the distance 724 may become progressively smaller from the most distal portion 726 of the legs 722 towards a more proximal portion 728 of the legs 722, so as to provide a tapered engagement surface 730 (FIG. 6D) to interact with the base 614*c*. Such a tapered engagement surface 730 may provide a progressively tighter engagement with the base 614*c* as the first endoscope 640 is coupled to the second endoscope 610. Thus, the engagement surface 730 of the legs 722, by virtue of contacting at least a portion of the base 614*c*, helps to stabilize and rigidly hold or couple the first endoscope 640 to the second endoscope 610.

Methods of using the embodiments of the endoscopes in FIGS. 6A-6E to perform a dual-endoscope procedure are also disclosed. The method includes obtaining a first endoscope and a second endoscope as described above. The method further includes directing the first shaft to a target region, such as within a duodenum adjacent the Ampulla of Vater. The method also includes directing the second shaft through the accessory passage into the common bile duct. The method also includes conducting one or more of endoscopic retrograde cholangiopancreatography, endoscopic retrograde cholangiography, and cholangioscopy. Such procedures and methods involve manipulating the first shaft and the second shaft, respectively, via controls, typically manipulating the controls of the first endoscope with one hand and manipulating the controls of the second endoscope with the other hand.

FIGS. 7A-7D show another embodiment of a connection structure of a miniscope (first endoscope) configured for securely and removably mounting the miniscope handle to an accessory port channel of a second endoscope in a manner axially aligning the miniscope shaft passage with the second endoscope's accessory channel to provide a path of communication for the miniscope shaft therethrough. Those of skill in the art will appreciate that the structures described and illustrated with reference to this embodiment provide for a quick-connect/release mechanism that is configured to (i.e., effectively will, as herein defined) securely, rigidly, and removably couple a first endoscope to a second endoscope, where a very few small simple movements by a user will effect connection with or release from, as needed, of the first endoscope and second endoscope.

Figure 7A:
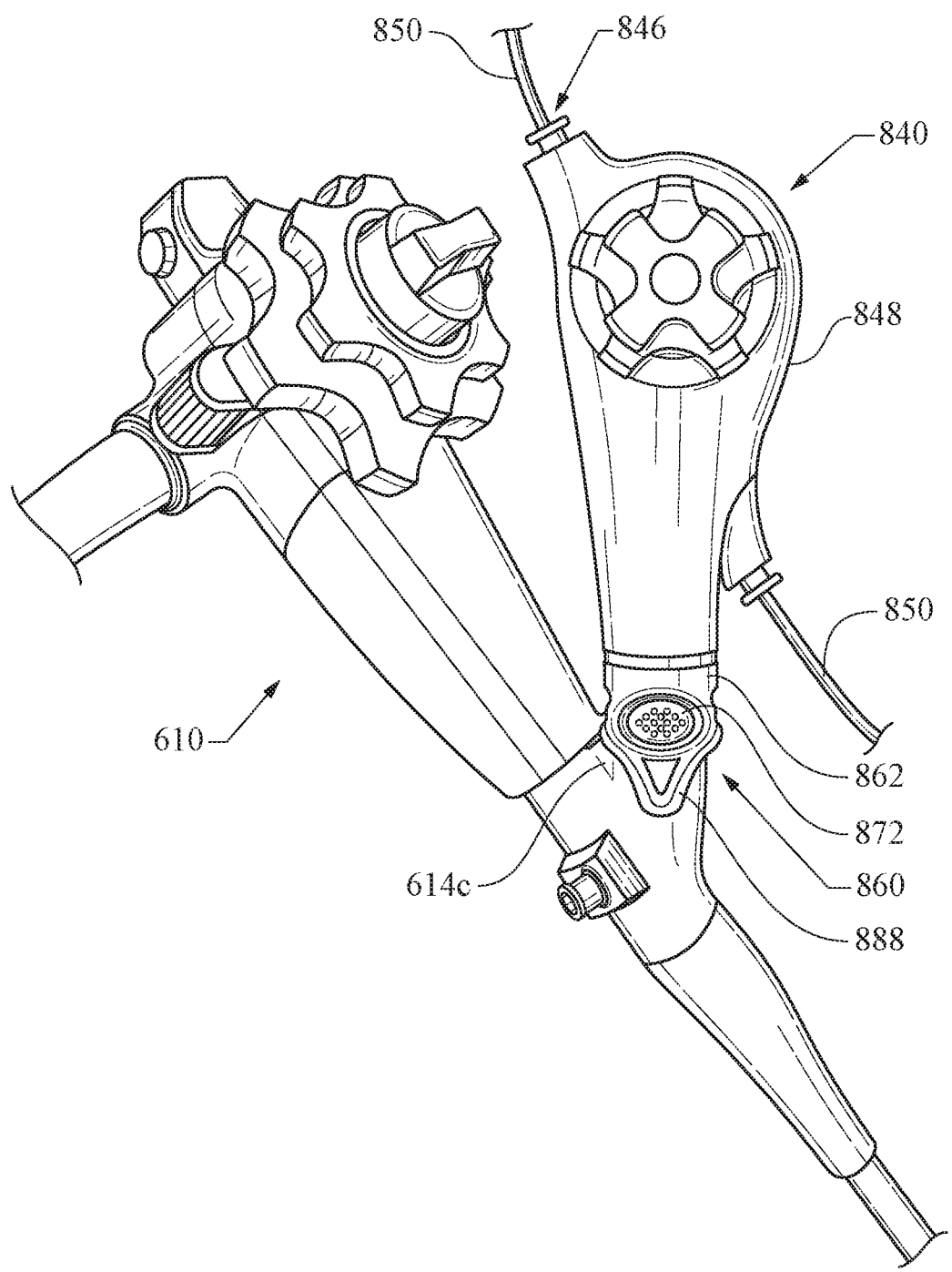
FIGS. 7A-7D show another embodiment of the present quick-connect/release connection structure.
Figure 7B:
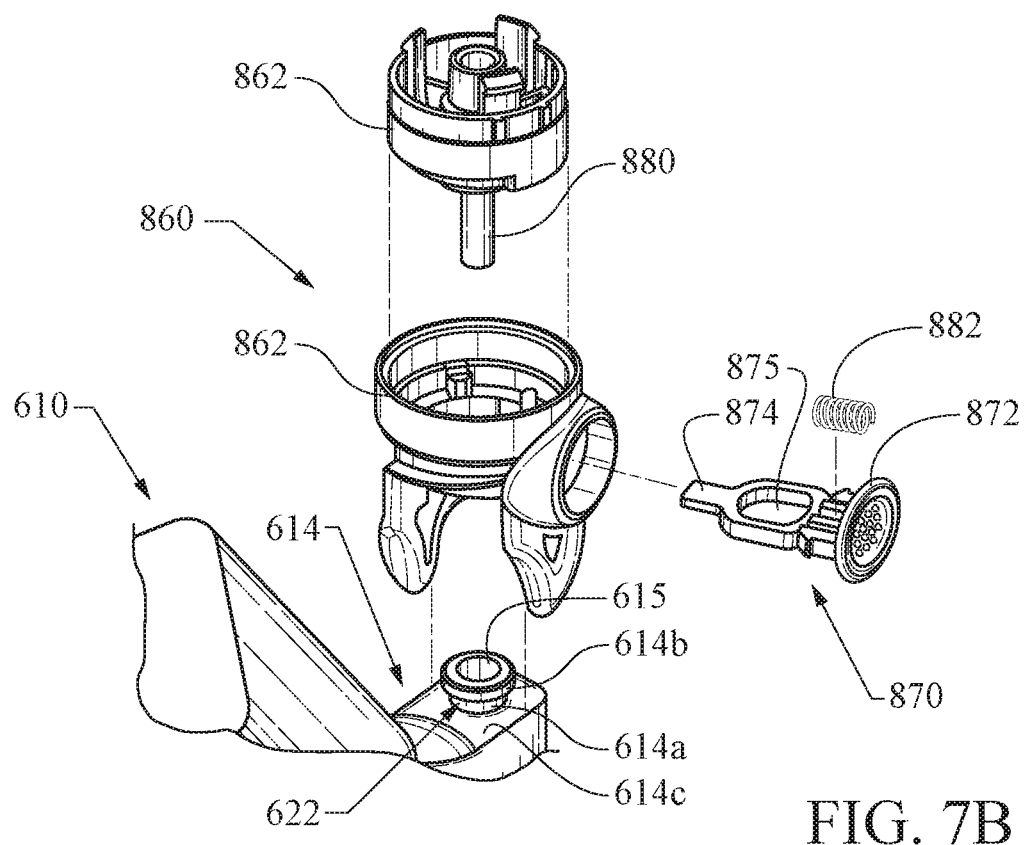
Figure 7C:
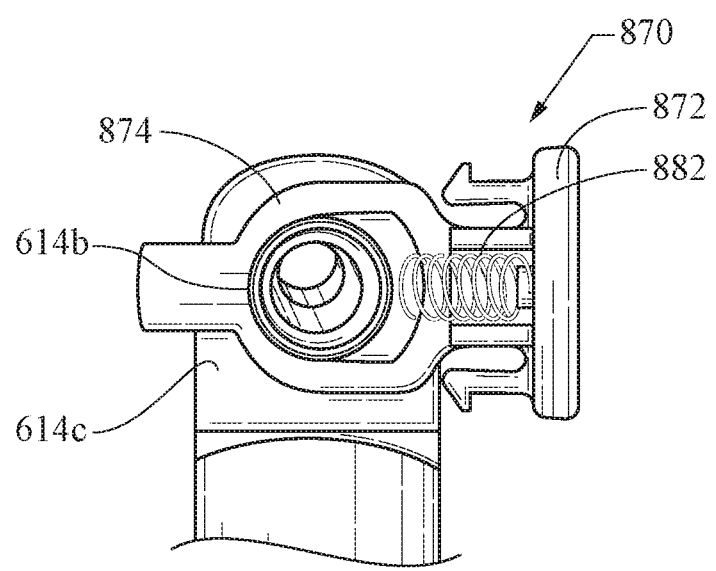
Figure 7D:
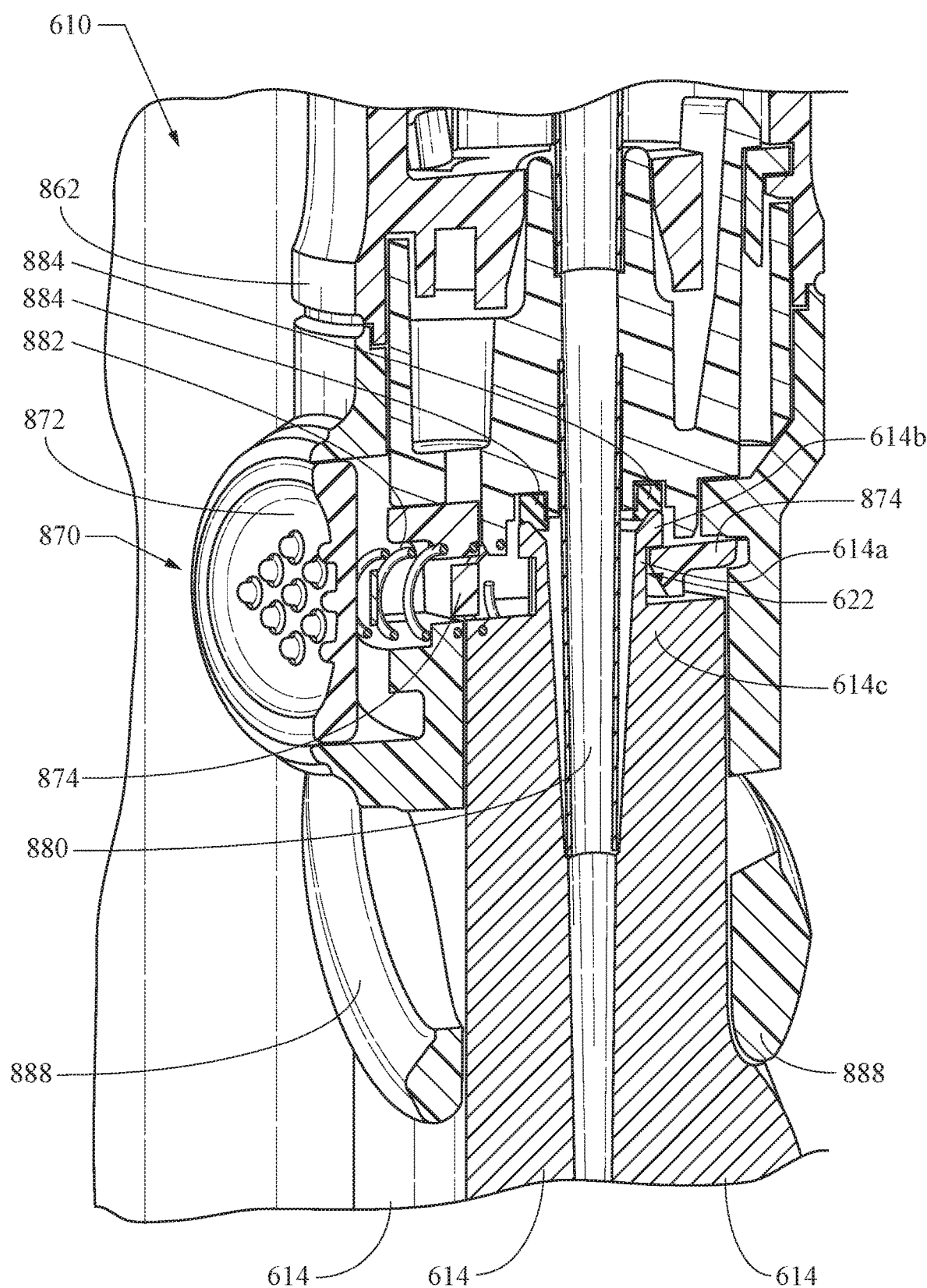

FIG. 7A shows an embodiment of a connection structure/endoscope locking mechanism 860 as part of a first endoscope, or miniscope 840 that is securely and rigidly, but removably and adjustably, attached to a second, larger endoscope 610. FIGS. 7B-7D show the structure and function of the first connection structure 860. The elements of the larger endoscope 610 are identified with the same reference numbers as used above in regard to FIGS. 6A-6E. The basic principle of operation is the same in this embodiment, but the direction of engagement is opposite from the embodiment of FIGS. 6A-6E, as will be apparent to those of skill in the art, where both embodiments provide for firm, secure, and removable attachment of a first endoscope to a second endoscope with a fluid-patent connection that allows essentially no movement of the first endoscope relative to the second endoscope the connection structure with its internal endoscope locking mechanism is actuated/engaged. Other than for the larger scope and the general number for the connection mechanism/endoscope locking mechanism 860, the reference numbering convention used in FIGS. 7A-7D does not follow the "like numbering" comment above.

As shown in FIGS. 7A and 7D, when the connection structure 860 is engaged to the port 614 (see FIG. 7B), a passage through the miniscope handle from the port 846 (see FIG. 7A) and accommodating the shaft body 850 is aligned with and secured to the accessory channel 615 of the larger scope 610. The perspective cross-sectional view of FIG. 7D shows the internal construction details. This alignment will allow operation of the miniscope catheter shaft body 850 that is looped around and through the miniscope handle port 846, so that it aligns with and readily passes through the miniscope handle body 848 into the accessory channel 615. For clarity and simplicity of illustration FIGS. 7B-7D do not show the miniscope shaft 850, instead focusing upon the endoscope locking mechanism.

FIG. 7B shows an exploded view of the components of a first connection structure illustrated as an endoscope locking mechanism 860. FIG. 7C shows just the interface of the locking member 870 with the mounting port 614 above the base 614*c*.

As shown in FIG. 7A and more particularly shown with reference to FIGS. 7B-7D, an endoscope locking mechanism 860 may include a hub 862 and a locking member 870 that includes an externally-visible tab-actuation element, embodied here as a button portion 872, and a generally flat planar tab portion 874 extending out from the button portion. The tab portion 874 includes an aperture 875 therethrough that is dimensioned to receive/pass over the flanged annular lip 614*b* of the mounting port 614. The thickness of the tab portion 874 is dimensioned to fit securely below the underside surface of the annular lip 614*b*, where the inner diameter face of the aperture 875 engages against the outer diameter face 622 (as identified in FIG. 6E) of the tubular element 614*a* of the mounting port 614. A biasing element 882 (shown here as a spring, but able to be embodied as any suitable biasing means) biases the locking member 870 relative to the hub 862 in a direction away from the center of the aperture 875 along the plane of the tab 874 and toward the button 872. It should be appreciated that the bias could be opposite with a rearrangement of elements more internally similar to the other embodiment described above. The tab-actuation element may otherwise be embodied as a knob, lever, or any other mechanical means that those of skill in the art will appreciate as being appropriate for engaging and disengaging the tab portion 874 for locking and unlocking the mechanism 860, particularly with respect to a second endoscope.

A tubular engagement extension 880 permanently affixed in the hub 862 of the connection structure/endoscope locking mechanism 860 is received into the mounting port 614. A sealing O-ring 884 (see FIG. 7D) is provided to facilitate a fluid-patent seal between two engaged endoscopes. The hub 862 may be constructed of one or several components, and the particular elements of the hub shown in the drawings should not be seen as limiting, but rather as one means of providing a hub that receives a locking member 870 (including button 872 and tab 874) and a biasing element 882 in a manner aligning the locking element effectively with the mounting port 614. As such the two-piece hub illustrated is one of many ways that those of skill in the art may construct a locking mechanism within the scope of, and as informed by, the present embodiments and claims.

The hub 862 may include one or more leg elements 888 that are dimensioned and configured to conform and fit firmly and securely against opposing surfaces of a mounting port base of another endoscope. These leg elements 888 may be solid, or may have a "loop" configuration as shown. Those of skill in the art will appreciate that the specific dimensions of the leg(s) 888 and other elements of the locking mechanism 860 may be configured for secure, fluid-patent connection with particular other endoscopes. These legs 888 will engage along the sides of the mounting base 614c in a manner that further secures engagement of the two scopes 610, 840 when the locking mechanism is actuated, such that movement of the scopes 610, 840 along that joint is essentially prevented unless/until the button 872 is depressed to release the engagement.

The top-down view of FIG. 7C shows one possible shape of the tab aperture 875, which maximizes the contact between the upper side of the tab portion 874 with the underside 632 of the flanged annular lip 614b that prevents movement between the two scopes along a longitudinal axis of the port 614 (the "Z-axis" of FIG. 7C). In the configuration shown, the engagement of the tab 874 with below the annular ring 614b of the port 614 is on the side opposite the button 872, so that the movement required to allow passage of the annular flanged lip 614b through the aperture 875 to attach or detach (lock/engage or unlock/disengage) one scope from another with the locking mechanism 860 simply is depressing the button 872 along the long axis of the locking member 870 (which is centrally and longitudinally coplanar with the generally flat plane defined by the tab 874. The combination of contact between the inner-diameter face of the aperture 875 with the outer-diameter surface 622 of the tubular body 614a, the contact of the hub 862 and the tab 874 with the upper face of the mounting base 614c, and the contact of the legs 888 with the lateral sides of the mounting base 614c provide a firm and secure removable connection between the scopes that will permit essentially no movement (meaning that, along the connection, the handles will not move relative to each other during normal operation when the locking mechanism is engaged/actuated, which normal operation conditions will readily be understood by those of skill in the art as including typical cholangioscopy procedures or other procedures using a miniscope attached to a larger scope or other mounting base). Other aspects of structure and operation will be clear to those of skill in the art with reference to the drawing figures and text for this embodiment and the embodiment described above with reference to FIGS. 6A-6E.

Those of skill in the art will appreciate that embodiments not expressly illustrated herein may be practiced within the scope of the claims, including that features described herein for different embodiments may be combined with each other and/or with currently-known or future-developed technologies while remaining within the scope of claims. Except where expressly set forth in said claims, embodiments presently disclosed and claimed are directed to a single endoscope and its connection mechanisms, while a second endoscope is referenced by way of environment/context for the connection mechanism's structure and function (except that certain claims specifically cite a dual-scope structure and other claims expressly claim the structure of the second endoscope as an addition to the connection mechanism of a first scope).

Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. In certain claims, a second endoscope is used as a reference structure only, but it is expressly intended that no structural element of the second endoscope is claimed as the present embodiment is directed to a connection mechanism and a first endoscope including a connection mechanism, which structure is independent of a second endoscope to which the first endoscope may be connected by the mechanism. This is grammatically expressed in the claim language, in keeping with canons of claim construction by using only "general articles" ("a/an") to refer to the second endoscope and its components rather than "specific articles" ("the") so that those of skill in the art will clearly understand when and where the second endoscope either is claimed or is not claimed, without introducing any indefiniteness about the scope of such claims. For example, the phrase "a second endoscope tubular element" will be understood to indicate only an unclaimed reference structure that provides more definite structural and functional clarity for elements of the claimed first endoscope and claimed connection mechanism without requiring any structure of a second endoscope actually to be present.

It should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

I claim:

1. An endoscope locking mechanism, said mechanism comprising:
   a hub member of a first endoscope dimensioned and configured to mate directly and removably in contact with a mounting port base of another endoscope by means of a locking member including a flat planar tab portion defining a major plane of the locking member and extending out from a tab-actuation element, where the tab portion includes a tab portion aperture therethrough that is dimensioned to receive and engage removably around and below a flange of a flanged tubular port of the mounting port base, and by means of a tubular engagement extension dimensioned to be removably received into a tubular body portion of the flanged tubular port; and
   a biasing element that biases the locking member relative to the hub member along the major plane of the locking member and across a longitudinal axis of the hub member, where the major plane includes an aperture-defining structure that is biased by the biasing element into contact with the tubular body portion of the flanged tubular port.

2. The endoscope locking mechanism of claim 1, where the biasing element biases the locking member relative to the hub member in a direction toward the tab-actuation element.

3. The endoscope locking mechanism of claim 1, where the biasing element biases the locking member relative to the hub member in a direction away from the tab-actuation element.

4. The endoscope locking mechanism of claim 1, where the hub member comprises one or more leg elements dimensioned and configured to conform and fit against opposing surfaces of the mounting port base of the another endoscope.

5. The endoscope locking mechanism of claim 1, being comprised by the first endoscope, and further comprising a state of being engaged with the another endoscope of claim 1;
- where the another endoscope includes the flanged tubular port extending from the mounting port base of the another endoscope;
- where the flanged tubular port includes a terminal flange having a larger diameter than the tubular body portion between the terminal flange and the mounting port base,
- where the tab portion aperture is dimensioned to pass over the terminal flange and is biased by the biasing element so that an inner diameter surface of the tab portion aperture engages around the tubular body portion and an upper side surface of the tab portion engages against an underside of the terminal flange, and
- said endoscope locking mechanism configured where depressing the tab-actuation element relative to the hub member moves the tab portion aperture into an alignment relative to the terminal flange that the tab portion aperture freely passes over the terminal flange to release and remove the first endoscope from engagement with the another endoscope.

6. A dual medical endoscope system comprising:
- the first endoscope comprising the endoscope locking mechanism of claim 1;
- the another endoscope configured to be a second endoscope, larger than the first endoscope, where the second endoscope comprises
  - the flanged tubular port including the tubular body portion extending from the mounting port base of the second endoscope; and
  - a terminal flange having a larger diameter than the tubular body portion and separated from the mounting port base by a length of the tubular body portion; and
- where the first endoscope includes the tubular engagement extension removably received into the tubular body portion.

7. The dual medical endoscope system of claim 6, wherein the first endoscope further comprises one or more leg elements dimensioned and configured to conform and fit against opposing side surfaces of the mounting port base of the second endoscope.

8. The dual medical endoscope system of claim 6, wherein the locking member is configured to be actuated by depressing the tab-actuation element along the major plane of the locking member.

9. The dual medical endoscope system of claim 6, wherein the first endoscope includes a catheter shaft body extending out of a handle body of the first endoscope, looped around so as to extend through the handle body, and further extending into the flanged tubular port of the second endoscope.

10. The endoscope locking mechanism of claim 1, wherein the locking member is configured to be actuated by depressing the tab-actuation element along the major plane of the locking member.

* * * * *